United States Patent [19]

Thiem

[11] Patent Number: 5,639,454
[45] Date of Patent: Jun. 17, 1997

[54] RECOMBINANT BACULOVIRUS WITH BROAD HOST RANGE

[75] Inventor: Suzanne M. Thiem, Okemos, Mich.

[73] Assignee: Board of Trustees operating Michigan State University, East Lansing, Mich.

[21] Appl. No.: 417,822

[22] Filed: Apr. 6, 1995

[51] Int. Cl.$^6$ .......................... A01N 63/00; C12N 15/63; C12N 15/86
[52] U.S. Cl. ................... 424/93.2; 435/69.1; 435/172.3; 435/235.1; 435/320.1; 435/348
[58] Field of Search .......................... 435/69.1, 172.1, 435/172.3, 320.1, 240.2; 536/23.1, 23.72; 424/93.6, 93.2

[56] References Cited

U.S. PATENT DOCUMENTS

| | | | |
|---|---|---|---|
| 4,745,051 | 5/1988 | Smith et al. | 435/69.51 |
| 5,004,687 | 4/1991 | Miller | 435/69.1 |
| 5,180,581 | 1/1993 | Miller et al. | 424/93.2 |
| 5,266,314 | 11/1993 | Maeda | 424/93.2 |
| 5,352,451 | 10/1994 | Miller et al. | 424/93.2 |

OTHER PUBLICATIONS

Groner, A., Specificity and safety of baculoviruses., In Granados, R.R. and Federici, B.A. (eds), CRC Press, Boca Raton, FL, The biology of baculoviruses. vol. I, pp. 177–202 (1986).
Summers, M.D., et al., A manual of methods for baculovirus vectors and insect culture procedures. Texas. Agri. Exp. Station Bulletin No. 1555 (1987).
Bonning, B.C., et al., Insect Biochem. Molec. Biol. 22:453–458 (1992).
Carbonell, et al., Gene 73:409–4 (1988).
Eldridge, R., et al., Appl. Environ. Microbiol. 58:1583–1591 (1992).
Hammock, B.D., et al., Nature (London) 344:458–461 (1990).
Maeda, S., Biochem. Biophys. Res. Commun. 165:1177–1183 (1989).
Maeda et al., Virol. 184:777–780 (1991).
Martens, J. W. M., et al., Appl. Environ. Microbiol. 56:2764–2770 (1990).
McCutchen, B. F., et al., Bio/Technology 9:848–852 (1991).
Merryweather, A. T., et al., J. Gen. Virol. 71:1535–1544 (1990).
Stewart, L. M., et al., Nature (London), 352:85–88 (1991).
Tomalski, M.D. and Miller, L.K., Nature (London) 352:82–85 (1991).
Tomalski, M.D. and Miller, L.K., Biotechnology 10:545–549 (1992).
O'Reilly, D. R. and Miller, L.K., Science 245:1110–1112 (1989).
O'Reilly, D. R., et al., Bio/Technology 9:1086–1089 (1991).
Goodwin, R. H., et al., In Vitro. 14:485–494 (1978).
McClintock, J. T., et al., J. Virol. 57:197–204 (1986).
McClintock, J. T., et al., Virus Res. 7:351–364 (1987).
Lee, H. H., et al., J. Virol. 27:754–767 (1978).
Slavicek, et al, J. Invertebr. Pathol. 59:142–148 (1992).
Felgner, P.T., et al., Proc. Natl. Acad. Sci. U.S.A. 84:7413–7417 (1987).
Vaughn, J. L., et al., In Vitro., 13:213–217 (1977).
Devereux, J., et al., Nucleic Acids Res. 12:387–395 (1984).
Cherbas, L et al., Insect Biochem. Molec. Biol. 23:81–90 (1993).
Weyer, U., et al., J. Gen. Virol. 71:1525–1534 (1990).
Wang, X., et al., Gene 100:131–137 (1991).
Vlak, J.M., et al., Expression of cauliflower mosaic virus gene I using a baculovirus vector based upon the p10 gene and a novel selection mehtod p. 312–320 (1990).

Primary Examiner—David Guzo
Attorney, Agent, or Firm—Ian C. McLeod

[57] ABSTRACT

Insect control agents comprising a gene encoding a protein that affects the host range of baculoviruses. A unique gene encoding a protein of 25.7 kdal, p25.7, isolated from a baculovirus from the gypsy moth, Lymantria dispar nuclear polyhedrosis virus, that affects the host range of baculoviruses is disclosed. This "host range gene" allows a second baculovirus, Autographa californica nuclear polyhedrosis virus, to replicate in an insect cell line that will not normally support its replication. Methods for producing the insect control agents are included. A recombinant Autographa california nuclear polyhedrosis virus, in which the p25.7 gene has been inserted, was demonstrated to replicate in both a cell line and an insect species that the unaltered Autographa californica nuclear polyhedrosis virus does not infect. The recombinant Autographa californica nuclear polyhedrosis virus also shows increased virulence towards insects that are susceptible to infection by unaltered virus as demonstrated by a significant reduction in the dose of virus needed to kill 50% of the infected insect larvae (LD50).

21 Claims, 8 Drawing Sheets

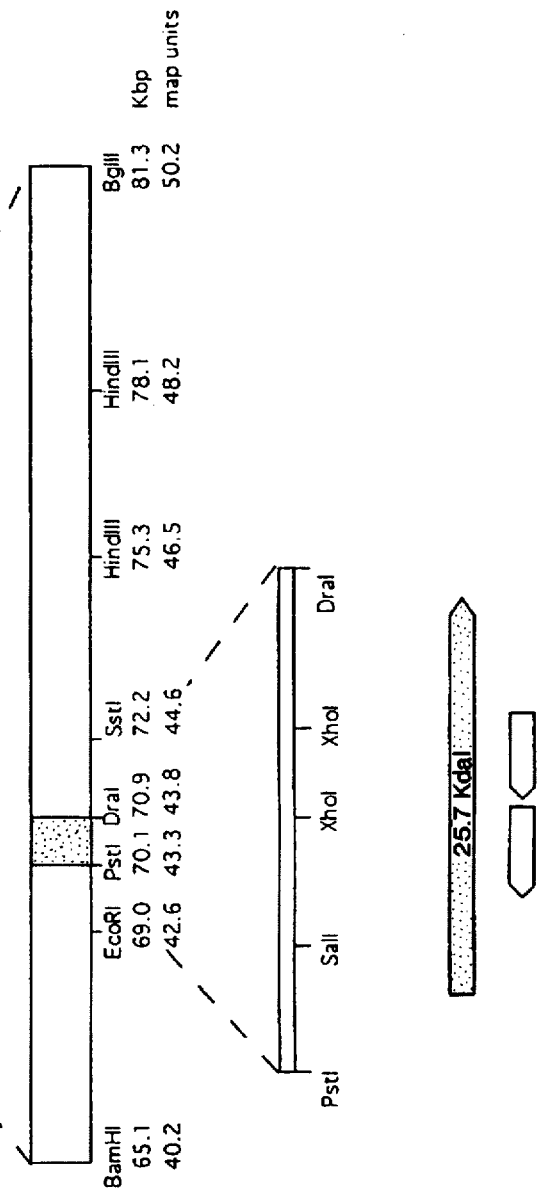

```
          ---------+---------+---------+---------+---------+---------+
                                           *
  1 CTGCAGCGTGTGTAACTGTACTTGCAATTGCGACCCGTGTCAGTACACGCCAGCGCACAG   60

61 TGCGGAGCGAACGCGACCAGCGCCGCGCAGCGAGACGAATATCGATTCATTTTATTTAGC  120

121 GCGCGCCGACGACCATGGGCATGGACGCCGAGTTTTTCGTGGACGGCGAACGCGTGGACA  180
                MetGlyMetAspAlaGluPhePheValAspGlyGluArgValAspSer  -

181 GCTACAAGTGCACCGGGCGGTGGTCCGCCATCGTCGACGTGCGCCACCGTCCCGCCTTGA  240
     TyrLysCysThrGlyArgTrpSerAlaIleValAspValArgHisArgProAlaLeuThr  -

241 CGGTGCGCTACCGGTACGAGCGCGGCTACGGCCACTACGCGCTCTTTGTTTATTTTCGAC  300
     ValArgTyrArgTyrGluArgGlyTyrGlyHisTyrAlaLeuPheValTyrPheArgHis  -

301 ACGTGGCCACCGGCATGCTGGAGACGGAGCGCGTGGACGTCGCCGACCGCGACCGCGTCG  360
     ValAlaThrGlyMetLeuGluThrGluArgValAspValAlaAspArgAspArgValVal  -

361 TGCCCGTGCCCGAAGAGTGGCTCGAGTACATCGACGACGACGACGAGGAGCGCGAACGCC  420
     ProValProGluGluTrpLeuGluTyrIleAspAspAspAspGluGluArgGluArgGln  -

421 AAGTGGAGGTGTTCGTGTGCATGAAGGGCGACTGCTACGCCCACGACGGCCCCCTGTTCG  480
       ValGluValPheValCysMetLysGlyAspCysTyrAlaHisAspGlyProLeuPheVal -

481 TCTCCGAGGCGTCCAAATGGTGCAGCCGCGAGCCCGAACACGTTCGCATCAGAGACTCGC  540
     SerGluAlaSerLysTrpCysSerArgGluProGluHisValArgIleArgAspSerPro  -

541 CGCTCGAGGCCGTGCGACAAATCAAGTGCGCGGAGGACGTGTTCGCGTTCGTCGAAGCGT  600
     LeuGluAlaValArgGlnIleLysCysAlaGluAspValPheAlaPheValGluAlaPhe  -

601 TCATGCGGATCGAAGAGGGCGAGTACGCGTGGCGCGATCCGCTTGTGATCGACCAATTAA  660
     MetArgIleGluGluGlyGluTyrAlaTrpArgAspProLeuValIleAspGlnLeuAsn  -

661 ACGACCAAGAACTGGCCTCGATCGAGAAGGTTTTCGCCTCGACGGTGTGGAACTATTATG  720
     AspGlnGluLeuAlaSerIleGluLysValPheAlaSerThrValTrpAsnTyrTyrGlu  -

721 AAAAAGTTAACGCGCGACCGGTTTTGACCTTTGCCGAAAATTATTTGAAGAAATTAAATG  780
     LysValAsnAlaArgProValLeuThrPheAlaGluAsnTyrLeuLysLysLeuAsnGlu  -

781 AAAGTTTGTAATGTTATTATAGGATCTCGGTGCGTATAAATATTTAATAAAATTT       835
     SerLeu  *
```

FIG. 3

Titer on Ld652Y

Titer on Sf21

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 835
( B ) TYPE: Nucleic Acid (C) STRANDEDNESS: Single
(D) TOPOLOGY: Linear (ii) MOLECULE TYPE: DNA (iii) HYPOTHETICAL: No (iv) ANTI-SENSE: No (v) FRAGMENT TYPE:

(vi) ORIGINAL SOURCE:
(A) ORGANISM: Lymantria dispar
(B) STRAIN: N/A
(C) INDIVIDUAL ISOLATE: N/A
(D) DEVELOPMENTAL STAGE: N/A
(E) HAPLOTYPE: N/A
(F) TISSUE TYPE: N/A
(G) CELL TYPE: N/A
(H) CELL LINE: N/A
(I) ORGANELLE: N/A (vii) IMMEDIATE SOURCE: N/A (viii) POSITION IN GENOME: N/A (ix) FEATURE:
(A) NAME/KEY: protein encoding DNA
(B) LOCATION:
(C) IDENTIFICATION METHOD: sequencing
(D) OTHER INFORMATION: DNA encoding protein
for increasing host
range (x) PUBLICATION INFORMATION:

(xi) SEQUENCE DESCRIPTION: SEQ ID NO:1:

```
CTGCAGCGTG TGTAACTGTA CTTGCA (v) FRAGMENT TYPE:

(vi) ORIGINAL SOURCE:
  (A) ORGANISM: Lymantria dispar
  (B) STRAIN: N/A
  (C) INDIVIDUAL ISOLATE: N/A
  (D) DEVELOPMENTAL STAGE: N/A
  (E) HAPLOTYPE: N/A
  (F) TISSUE TYPE: N/A
  (G) CELL TYPE: N/A
  (H) CELL LINE: N/A
  (I) ORGANELLE: N/A (vii) IMMEDIATE SOURCE: N/A (viii) POSITION IN GENOME: N/A (ix) FEATURE:
  (A) NAME/KEY: protein encoded by DNA
  (B) LOCATION:
  (C) IDENTIFICATION METHOD: sequencing
  (D) OTHER INFORMATION: protein
       for increasing host
       range encoded by SEQ ID NO:1

(x) PUBLICATION INFORMATION:

(xi) SEQUENCE DESCRIPTION: SEQ ID NO:2:

```
                        Met Gly Met Asp Ala Glu Phe Phe Val Asp Gly Glu Arg
                                         5                   10
Val Asp Ser Tyr Lys Cys Thr Gly Arg Trp Ser Ala Ile Val Asp Val Arg
     15                  20                  25                  30
His Arg Pro Ala Leu Thr Val Arg Tyr Arg Tyr Glu Arg Gly Tyr Gly His
                     35                  40                  45
Tyr Ala Leu Phe Val Tyr Phe Arg His Val Ala Thr Gly Met Leu Glu Thr
             50                  55                  60
Glu Arg Val Asp Val Ala Asp Arg Asp Arg Val Val Pro Val Pro Glu Glu
 65                  70                  75                  80
Trp Leu Glu Tyr Ile Asp Asp Asp Asp Glu Glu Arg Glu Arg Gln Val Glu
                 85                  90                  95
Val Phe Val Cys Met Lys Gly Asp Cys Tyr Ala His Asp Gly Pro Leu Phe
     100                 105                 110                 115
Val Ser Glu Ala Ser Lys Trp Cys Ser Arg Glu Pro Glu His Val Arg Ile
                 120                 125                 130
Arg Asp Ser Pro Leu Glu Ala Val Arg Gln Ile Lys Cys Ala Glu Asp Val
         135                 140                 145
Phe Ala Phe Val Glu Ala Phe Met Arg Ile Glu Glu Gly Glu Tyr Ala Trp
 150                 155                 160                 165
Arg Asp Pro Leu Val Ile Asp Gln Leu Asn Asp Gln Glu Leu Ala Ser Ile
                 170                 175                 180
Glu Lys Val Phe Ala Ser Thr Val Trp Asn Tyr Tyr Glu Lys Val Asn Ala
     185                 190                 195                 200
Arg Pro Val Leu Thr Phe Ala Glu Asn Tyr Leu Lys Lys Leu Asn Glu Ser
                 205                 210                 215
Leu
```

RECOMBINANT BACULOVIRUS WITH BROAD HOST RANGE

GOVERNMENT RIGHTS

This invention was made with government support from National Institutes of Health (Grant No. 1 R29 GM48608) and from the USDA Forest Service (Cooperative Agreement No. 23-816). The U.S. government has certain rights in this invention.

BACKGROUND OF THE INVENTION

1. Field of the Invention

The present invention relates to methods for improved baculovirus insecticides by expanding the host range against insect pests.

2. Description of Related Art

Baculoviruses are insect-specific viruses that can be used as microbial insecticides. They are considered an attractive alternative to chemical insecticides because in contrast to many chemicals they do not leave potentially harmful chemical residues in the environment nor do they harm vertebrate animals or beneficial insects. Baculovirus insecticides comprised of nuclear polyhedrosis viruses (NPVs), a subgroup of baculoviruses, were first registered by the U.S. Environmental Protection Agency in 1979. However several features of natural baculovirus isolates detract from their positive attributes as insecticides. One of these is a prolonged period between ingestion of the virus, the natural route of infection, and the cessation of insect feeding. Another is that baculoviruses have restricted host ranges, infectivity is usually limited to members of the same genus or family of the original host (Gröner, A., Specificity and safety of baculoviruses., In Granados, R. R. and Federici, B. A. (eds), CRC Press, Boca Raton, Fla., The biology of baculoviruses., Vol. I, pp 177-202 (1986)). The mechanisms that determine baculovirus host specificity are unknown. Because of this several different baculovirus insecticides may be required to control insect pests if several species are infesting a crop. Baculoviruses, in particular Autographa californica nuclear polyhedrosis virus (AcMNPV), have been studied intensively at the molecular level. As a result of these studies, methods have been developed which permit modification of these viruses by genetic engineering. Recently, a great deal of effort has been focused on the improvement of baculovirus insecticides. These efforts have focused primarily on reducing the time to stop insect feeding following ingestion of a virus. This has been accomplished by the insertion of genes for insecticidal proteins (Bonning, B. C., et al. Insect Biochem. Molec. Biol. 22:453–458 (1992); Carbonell, et al. Gene 73:409–418 (1988); Eldridge, R., et al. Appl. Environ. Microbiol. 58:1583–1591 (1992); Hammock, B. D., et al. Nature (London), 344:458–461 (1990); Maeda, S., Biochem. Biophys. Res. Commun. 165:1177–1183 (1989); Maeda et al, Virol. 184:777–780 (1991); Martens, J. W. M., et al, Appl. Environ. Microbiol. 56:2764–2770 (1990); McCutchen, B. F., et al., Bio/Technology 9:848–852 (1991); Merryweather, A. T., et al, J. Gen. Virol. 71:1535–1544 (1990); Stewart, L. M., et al, Nature (London), 352:85–88 (1991); Tomalski, M. D. and Miller, L. K., Nature (London), 352:82–85 (1991); Tomalski, M. D. and Miller, L. K., Biotechnology 10:545–549 (1992)) or by the deletion of a baculovirus gene, ecdysteroid UDP-glucosyl transferase (EGT), that prolongs insect feeding (O'Reilly, D. R. and Miller, L. K., Science 245:1110–1112 (1989); O'Reilly, D. R., et al., Bio/Technology 9:1086–1089 (1991)). In order to modify the host range of a baculovirus it is necessary to identify the genes that control baculovirus host range so that the viruses can be altered to infect a variety of insect pest species.

The NPVs that infect lepidopteran larvae, the caterpillar stages of moths and butterflies, produce two morphological forms of the virus. A budded form that spreads the virus to tissues within the insect is used for propagating virus in insect cells. An occluded form in which the virions are packaged within a protein crystal called polyhedra is the normal infection route for larvae. The polyhedra are composed primarily of a single polypeptide called polyhedrin. The virus is acquired when the caterpillars eat foliage that is contaminated with polyhedra. The polyhedra dissolve in the midgut of the insect and release the virions which then enter the midgut cells to begin the infection. In baculovirus expression systems that are used to produce large quantities of various proteins for research or to produce commercial products such as pharmaceuticals the polyhedron gene, which is not necessary for virus growth in cell culture, is replaced by the gene of the protein to be produced and no polyhedra are produced. However, baculovirus expression systems have also been developed that permit expression of a foreign gene while maintaining the polyhedrin gene and thus the ability to produce occluded viruses (polyhedra) for insecticidal use.

The prior art has described various recombinant baculovirus. U.S. Pat. Nos. 5,180,581 to Miller et al; 5,266,314 to Maeda and 5,352,451 to Miller et al describe various recombinant baculovirus including foreign DNA which provide insect control. U.S. Pat. No. 5,004,687 to Miller describes a vital expression vector for production of exogenous gene products in insects. Various promoters are used, such as Rous sarcoma virus long terminal repeat promoter (LTR-RSV) genes can include toxic genes. Endogenous promoters include early and delayed early promoters of AcMNPV. Also the polyhedron promoter was described. U.S. Pat. No. 4,745,051 to Smith and Summers describes a method for producing a recombinant baculovirus expression vector which expresses a gene in a host. This general method is used in the present invention and is not repeated in the present specification.

OBJECTS

It is an object of the present invention to provide a method and compositions wherein a baculovirus with a limited host range is enabled to have a broad host range. In particular the present invention provides a method wherein a novel host range DNA is inserted into DNA of a baculovirus with a limited host range. Further, it is an object of the present invention to provide a method and composition wherein a protein produced by the host range DNA is used to provide a broad host range to a limited host range baculovirus. These and other objects of the present invention will become increasingly apparent by reference to the following description and the drawings.

BRIEF DESCRIPTION OF THE DRAWINGS

FIG. 1 (Parts A–D) are diagrams of the LdMNPV genome showing the locations of the overlapping cosmid clones used in identifying p25.7 and the location of the gene encoding p25.7. FIG. 1A shows the BglII restriction map of the LdMNPV genome with respect to map units and kilobase pairs (kbp). FIG. 1B shows the location of each cosmid clone with respect to the physical map of LdMNPV. FIG. 1C shows the map location of the PstI-DraI restriction fragment comprising the host range gene, p25.7. FIG. 1D shows the open reading frames with the PstI-DraI DNA fragment located 43.3–43.8 map units.

FIG. 2 (Parts A to C) are diagrams of cloned LdMNPV DNA fragments that were tested for the ability to promote the replication of AcMNPV in Ld652Y cells. Clones that promote AcMNPV replication are designated by a "+" symbol in the column "Virus Production".

FIG. 3 shows the nucleotide sequence (SEQ ID NO:1) of the 835 bp PstI-DraI DNA fragment cloned into the PstI and EcoRV sites in pBluescript to obtain pBSLdPD and the translation of the 654 bp open reading frame within this fragment a polypeptide of 218 amino acid residues with a predicted molecular weight of 25674.64 Dal, p25.7. Transcription of the gene initiates within a TCAGT motif indicated by underlining with the majority of the transcript initiating at the "C" indicated by an asterisk.

FIG. 4 (Parts A to C) is a schematic showing the principles of genetically engineering baculoviruses.

FIGS. 5 (Parts A to C) diagrams the construction of a recombinant AcMNPV expressing the p25.7 gene.

FIG. 6 (Parts A to B) are graphs of budded virus production in AcMNPV- and vAcLdPD-infected Ld652Y and SF21 cells.

DESCRIPTION OF PREFERRED EMBODIMENTS

Figure 2A:
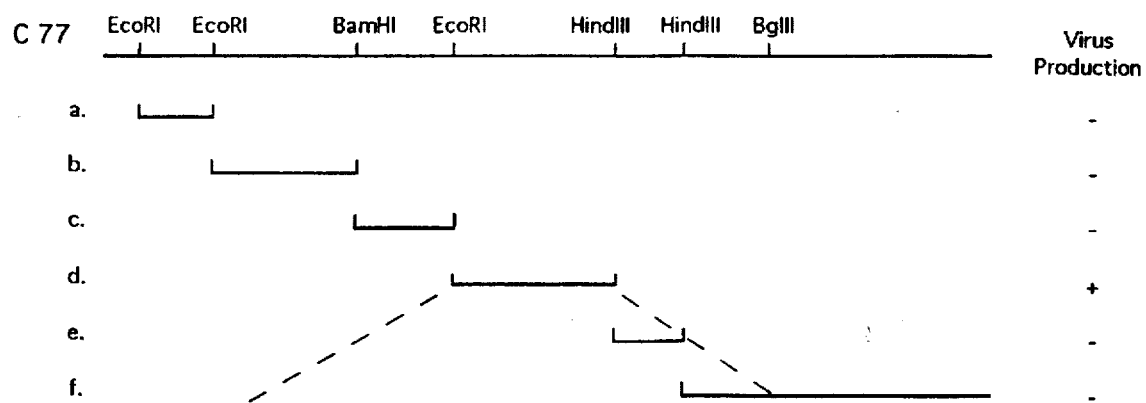
FIG. 2A shows subclones of cosmid clone C77 (shown in FIG. 1B).

The present invention relates to an isolated segment of DNA of a baculovirus encoding a protein sufficiently duplicative of that set forth in SEQ ID NO:1 so as to provide a broad host range in an insect when the DNA is incorporated into a baculovirus with a limited host range in the insect. SEQ ID NO:1 shows the protein and SEQ ID NO:2 shows the DNA encoding the protein.

Further the present invention relates to an isolated segment of DNA which is a gene of a polyhedron baculovirus encoding a 25.7 kdal protein sufficiently duplicative of that DNA contained in Escherichia coli deposited as ATCC 97061 to provide a broad host range in an insect when the DNA is incorporated into a baculovirus with a limited host range in the insect.

Further still, the present invention relates to a recombinant vector containing a segment of DNA encoding an isolated segment of DNA of a baculovirus encoding a protein sufficiently duplicative of that set forth in SEQ ID NO:1 so as to provide a broad host range in an insect when the DNA is incorporated into a baculovirus with a limited host range in the insect.

Further still, the present invention relates to a recombinant vector containing a segment of an isolated segment of DNA which is a gene of a polyhedron baculovirus encoding a 25.7 kdal protein sufficiently duplicative of that DNA contained in Escherichia coli deposited as ATCC 97061 to provide a broad host range in an insect when the DNA is incorporated into a baculovirus with a limited host range in the insect.

The present invention also relates to a baculovirus containing a segment of DNA encoding a protein sufficiently duplicative of that set forth in SEQ ID NO:1 so as to provide a broad host range in an insect when the DNA is incorporated into a baculovirus with a limited host range in the insect.

The present invention also relates to a recombinant baculovirus containing DNA which is a gene of a polyhedron baculovirus encoding a 25.7 kdal protein sufficiently duplicative of that DNA contained in Escherichia coli deposited as ATCC 97061 to provide a broad host range in an insect when the DNA is incorporated into a baculovirus with a limited host range in the insect.

The present invention further relates to a method of inhibiting an insect which comprises exposing the insect to a recombinant baculovirus containing a segment of DNA of a baculovirus encoding a protein sufficiently duplicative of that set forth in SEQ ID NO:1 so as to provide a broad host range in the insect when the DNA is incorporated into a baculovirus with a limited host range in the insect.

The present invention also relates to a method of inhibiting an insect which comprises exposing the insect to a recombinant baculovirus containing a segment of DNA which is a gene of a polyhedron baculovirus encoding a 25.7 kdal protein sufficiently duplicative of that DNA contained in Escherichia coli deposited as ATCC 97061 to provide a broad host range in the insect when the DNA is incorporated into a baculovirus with a limited host range in the insect.

The present invention relates to a composition which comprises a protein as expressed by an isolated segment of DNA of a baculovirus encoding a protein sufficiently duplicative of that set forth in SEQ ID NO:1 to provide a broad host range in an insect when present with a baculovirus with a limited host range; and the baculovirus with the limited host range.

The present invention relates to a composition which comprises a protein derived from Escherichia coli ATCC 97061; and a virus which is Autographa californica.

The present invention further relates to a method of inhibiting an insect which comprises exposing the insect to a composition which comprises: a protein as expressed by an isolated segment of DNA of a baculovirus encoding a protein sufficiently duplicative of that set forth in SEQ ID NO:1 to provide a broad host range in an insect when present with a baculovirus with a limited host range; and the baculovirus with the limited host range so that the insect dies.

In the present invention a baculovirus gene that is able to expand the host range of a baculovirus to cell lines and insect larvae in which replication was previously limited is identified. The present invention provides methods for the use of this gene in insect control strategies. When the p25.7 gene is transferred to AcMNPV, it expands its host range enabling it to replicate in a cell line, Ld652Y, and in gypsy moth larvae which do not normally support AcMNPV replication. The p25.7 gene also increases the infectivity of AcMNPV against insects that it normally infects.

The present invention encompasses a broad range of insect control agents utilizing the protein, p25.7 or the p25.7 gene. The insecticides of the present invention permit baculoviruses to replicate in cells, tissues, or insect species in which the natural baculovirus isolate can not replicate. Insertion of the p25.7 gene into AcMNPV or other baculoviruses that lack this gene expands the virus host range and increasing the virulence and potency of these viruses in vivo against caterpillars that are pests of agricultural crops or forests, thus improving their properties as insecticides.

A general procedure for constructing recombinant baculoviruses expressing p25.7 for use as insecticides is discussed in Example 2.

EXAMPLE 1

Identification of the host range gene, p25.7, by the ability of transfected LdMNPV DNA to promote the replication of AcMNPV in a non-permissive cell line.

Insect cell lines have been developed that can be maintained in culture by serial passage for multiple generations. Many of these cell lines can support the replication of various insect baculoviruses. One of these cell lines, IPBL-Ld652Y (Goodwin, R. H., et al, In Vitro. 14:485–494 (1978)), supports the replication of LdMNPV, a baculovirus that infects the gypsy moth, and is routinely used to propagate this virus in vitro. The Ld652Y cell line does not support the replication of another baculovirus, AcMNPV, although AcMNPV does replicate in other insect cell lines. Replication of AcMNPV in Ld652Y cells has been described as "semipermissive" because a cytopathic effect is observed and several infected-cell-specific proteins are made when the cells are inoculated with AcMNPV (McClintock, J. T., et al, J. Virol. 57:197–204 (1986)). Superinfection of AcMNPV-infected Ld652Y cells with LdMNPV resulted in replication of AcMNPV (McClintock, J. T. and Dougherty, E. M., Virus Res. 7:351–364 (1987)). This suggested that AcMNPV was lacking a factor that was needed for replication in Ld652Y cells and that this missing factor or "helper function" could be provided by a second virus, LdMNPV, that could replicate in these cells.

It was determined that transfected LdMNPV DNA was able to promote replication of AcMNPV in Ld652Y cells in cotransfection assays in which DNA from both viruses was transfected into IBLB-Ld652Y cells. The strains of virus used were the L1 strain of AcMNPV (Lee, H. H. and Miller, L. K., J. Virol. 27:754–767 (1978)) and the A21 strain of LdMNPV (Slavicek, et al, J. Invertebr. Pathol. 59:142–148 (1992)). DNA was transfected using lipofectin (Life Technologies, Bethesda, Md.) using the procedure of Felgner, P. T., et al., Proc. Natl. Acad. Sci. U.S.A. 84:7413–7417 (1987). LD652Y cells were maintained in the laboratory in TC100 medium (Life Technologies, Bethesda, Md.) supplemented with 10% fetal bovine serum. Briefly, $4.5 \times 10^5$ Ld652Y cells were seeded into a 35 mm tissue culture plate and allowed to attach. For transfections 2.5 µg of DNA from each virus was mixed together in distilled water in a polystyrene test tube to a final volume of 50 µl then 50 µl of lipofectin was added and mixed. This solution was incubated at room temperature for 15 minutes. Just prior to adding the DNA and lipofectin preparation, the cell monolayers were washed gently 2× with 3 ml TC100 medium without bovine serum. After the final wash was removed, the cells were covered with 1.5 ml of TC100 medium without serum and the DNA lipofectin mixture was added to the monolayer dropwise around the plate. The plates were then incubated at 27° C. for 2 hours. After which time, the media was removed and the cells were fed with 3 ml of fresh TC100 medium supplemented with 10% fetal bovine serum. The plates were placed in a plastic bag along with a damp paper towel, to maintain humidity, and incubated at 27° C. for 5 days. Virus replication was scored by the presence of polyhedra in the nuclei of Ld652Y cells and by the production of budded virus in the cell supernatants. In most cases polyhedra were observed in positive reactions by 2 days after transfection of DNA. The presence of budded AcMNPV was determined by the ability of cell supernatants to infect IPLB-SF21 cells (Vaughn, J. L., et al, In Vitro., 13:213–217 (1977)) a cell line that supports AcMNPV but not LdMNPV replication. SF21 cells were seeded at $2 \times 10^6$ cells in 60 mm tissue culture plates and allowed to attach. Supernatants from transfections were collected into centrifuge tubes cleared of cell debris by low speed centrifugation, approximately 1000× g for 10 minutes. Medium was removed from the SF21 cell monolayers and 500 µl of cleared supernatants from transfections were added dropwise. The monolayers were rocked gently and after 1 hour incubation at room temperature the transfection supernatants were removed and the cells fed with 4 ml of TC100 medium supplemented with 10% fetal bovine serum. The plates were then incubated at 27° C. The cells were checked daily for the formation of polyhedra in the cell nucleus. Polyhedra were generally observed between one and two days after incubation with transfection supernatants.

The ability of transfected LdMNPV DNA to supply the missing factor for AcMNPV replication in Ld652Y cells made it possible to map the gene for the factor using transfection assays. In these assays AcMNPV DNA was co-transfected into Ld652Y cells along with various cloned pieces of LdMNPV DNA using the same procedures described in the previous paragraph except the quantity of each DNA species was reduced to 1 µg. Initial experiments were with an overlapping library of six cosmid clones, provided by J. M. Slavicek, USDA Forest Service (See FIG. 1B). Each of these clones are comprised of 28.5–45 Kb of LdMNPV DNA or between 17.6 and 27.8% of the LDMNPV genome, cloned into a cosmid cloning vector, Super-Cos 1 (Stratagene, LaJolla, Calif.). Two clones, C12 and C77, were able to, independently, promote replication of AcMNPV in these assays. If either clone was omitted, individually, from the transfection assay AcMNPV could replicate, however, if both clones were omitted AcMNPV replication did not occur (see TABLE 1). This suggested that the gene was located in the region of the LdMNPV genome where cosmid clones C12 and C77 overlap.

TABLE 1

| Transfected DNA | Viral Production |
| --- | --- |
| AcMNPV | − |
| LdMNPV | + |
| AcMNPV + LdMNPV | + |
| AcMNPV + C-15 | − |
| AcMNPV + C-2 | − |
| AcMNPV + C-12 | + |
| ACMNPV + C-77 | + |
| ACMNPV + C-38 | − |
| AcMNPV + C-64 | − |
| AcMNPV + C-63 | − |
| AcMNPV + All cosmids except C-12 | + |

TABLE 1-continued

| Transfected DNA | Viral Production |
| --- | --- |
| AcMNPV + All cosmids except C-77 | + |
| AcMNPV + All cosmids except C-12 and C-77 | – |

Production of virus in Ld652Y cells following transfection with viral and cosmid DNA into Ld652Y cells.

Figure 2B:
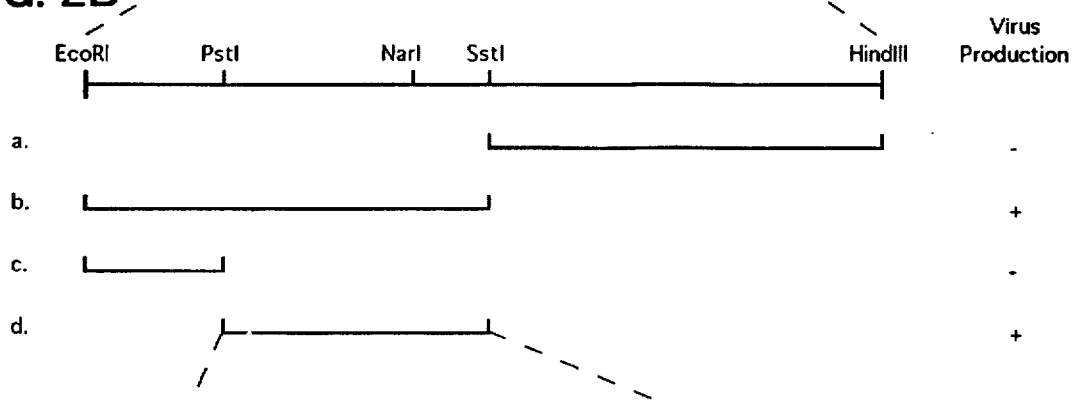
FIG. 2B shows subclones of the EcoRI-HindIII fragment that could promote AcMNPV replication.
Figure 2C:
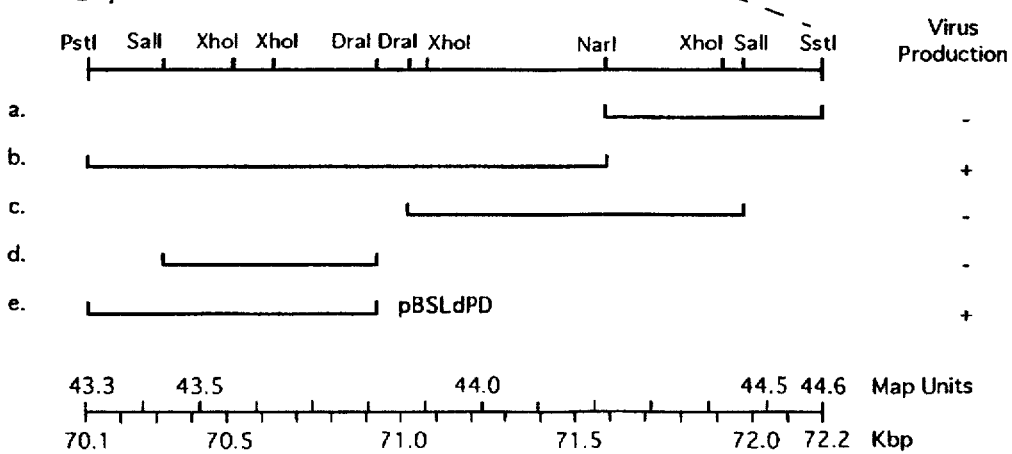
FIG. 2C shows subclones of the PstI-SstI subclone, shown in FIG. 2B, and identifies pBSLdPD an 835 bp PstI-DraI fragment, the smallest cloned DNA fragment that can promote AcMNPV replication in transfection assays. A scale in map units and Kbp indicates the location of the cloned DNA fragments in FIG. 2C with respect to the LdMNPV genome.

In order to more precisely map the host range gene it was necessary to subclone smaller pieces of the LdMNPV DNA from the overlapping region between cosmid C12 and C77. To accomplish this, cosmid C77 was cut into smaller fragments with restriction endonucleases and subcloned into Bluescript plasmids (Stratagene, LaJolla, Calif.) using standard cloning procedures. LdMNPV cosmid C77 was initially cleaved with EcoRI, HindIII, EcoRI and BamHI, or EcoRI and HindIII (see FIG. 2A), and the fragments subcloned into Bluescript plasmids to obtain six subclones. For example, to subclone the EcoRI-HindIII (FIGS. 1A, d and FIG. 2B) cosmid C77 and Bluescript KS+ were each cleaved with EcoRI and HindIII and the DNA was then mixed together, ligated, and used to transform bacteria, Escherichia coli, XL1-Blue, using standard DNA cloning methods known to those skilled in the art. Each of these subclones was tested in cotransfection assays as described above. Only one of these a 6.2 Kbp EcoRI-HindIII fragment (FIG. 1A, d. and FIG. 2B) was able to promote AcMNPV replication in Ld652Y cells in cotransfection assays. This fragment was cleaved into smaller fragments using PstI and SstI (see FIG. 2B) and subcloned into Bluescript plasmids. Two subclones (FIG. 2B, b. and d.) were able to promote AcMNPV replication in the cotransfection assays. The smaller of these two a 2.1 Kbp PstI-SstI fragment (FIG. 2B, d.) was further subcloned into Bluescript vectors following cleavage with NarI, DraI, or SalI and DraI, to obtain another subset of five clones (see FIG. 2C). The smallest fragment that could promote AcMNPV replication in IPLB-652Y cells, pBSLdPD, was an 835 bp PstI-DraI fragment. This region of the LdMNPV is located from 70.1 to 70.9 Kbp or between 43.3 and 43.8 map units with respect to the LdMNPV genome (see FIG. 1C). Plasmid pBSLdPd was deposited under the Budapest Treaty on Feb. 16, 1995 with the American Type Culture Collection as ATCC 97061.

The 835 bp fragment was sequenced by a polymerase chain reaction (PCR) approach using a CIRCUMVENT kit (New England Biolabs, Beverly, Mass.). The sequence of the 835 bp fragment is shown in FIG. 3. The sequence was compiled and analyzed using the University of Wisconsin Genetics Computer Group (GCG) programs (Devereux, J., et al, Nucleic Acids Res. 12:387–395 (1984)). There are three open reading frames within this region (see FIG. 1D). Two smaller open reading frames, and their putative promoter regions, transcribed right to left are entirely within the SalI-DraI fragment (see FIG. 2C, d.) that was unable to promote AcMNPV replication. Thus these reading frames are unlikely to encode the protein that promotes AcMNPV replication in Ld652Y cells. The remaining open reading frame, 654 bp, transcribed from left to right, encodes a polypeptide with a predicted molecular weight of 25674.64 Dal, p25.7 (FIG. 3). The open reading frame and predicted upstream regulatory sequences are entirely within the cloned LdMNPV PstI-DraI fragment that is sufficient for promoting AcMNPV replication. A TCAGT motif (underlined in FIG. 3) that is frequently used as a transcription initiation site in arthropods (Cherbas, L. and Cherbas, P., Insect Biochem. Molec. Biol. 23:81–90 (1993)) is identified within this upstream region. Primer extension analysis of RNA isolated from LdMNPV-infected Ld652Y cells indicates that mRNA transcription initiates within this TCAGT motif, primarily from the cytosine (marked by asterisk in FIG. 3). A comparison of both the PstI-DraI DNA sequences and the predicted amino acid sequence of the host range gene, p25.7, with current genetic sequence data bases, GENBANK, EMBL, and SWISSPROT, and with databases comprised of known protein motifs resulted in no matches. p25.7 appears to be a novel protein.

Thus in cell culture p25.7 can be supplied by transfection of a cloned copy of the LdMNPV PstI-DraI fragment, pBSLdPD, located between 43.3 and 43.8 map units with respect to the physical map of the A21 isolate of LdMNPV. pBSLdPD comprises the p25.7 coding sequence and the upstream sequences regulating its transcription. AcMNPV will replicate in Ld652Y cells when pBSLdPD DNA is transfected into cells along with AcMNPV DNA.

EXAMPLE 2

Methods for constructing recombinant baculoviruses that express the p25.7 gene.

Figure 4A:
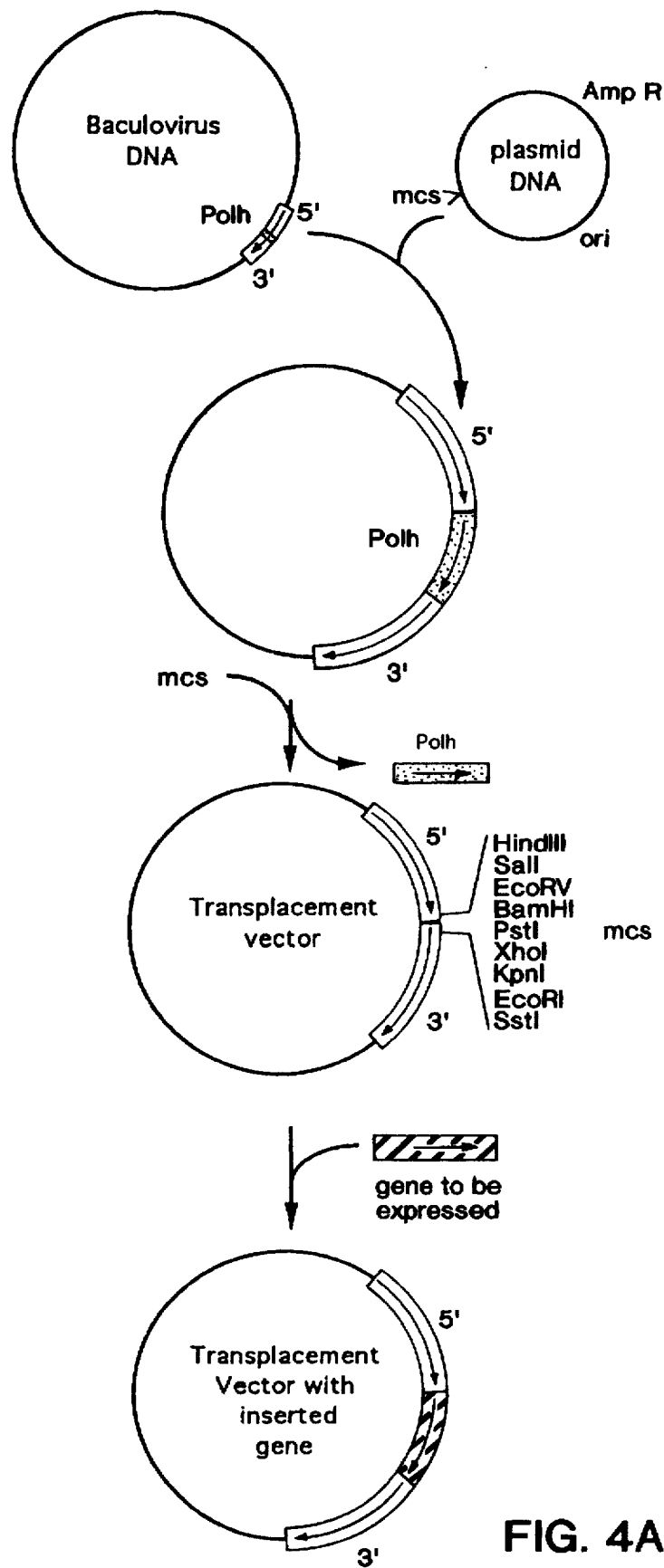
FIG. 4A depicts the construction of a typical baculovirus transplacement vector and insertion of a gene to be expressed.
Figure 4B:
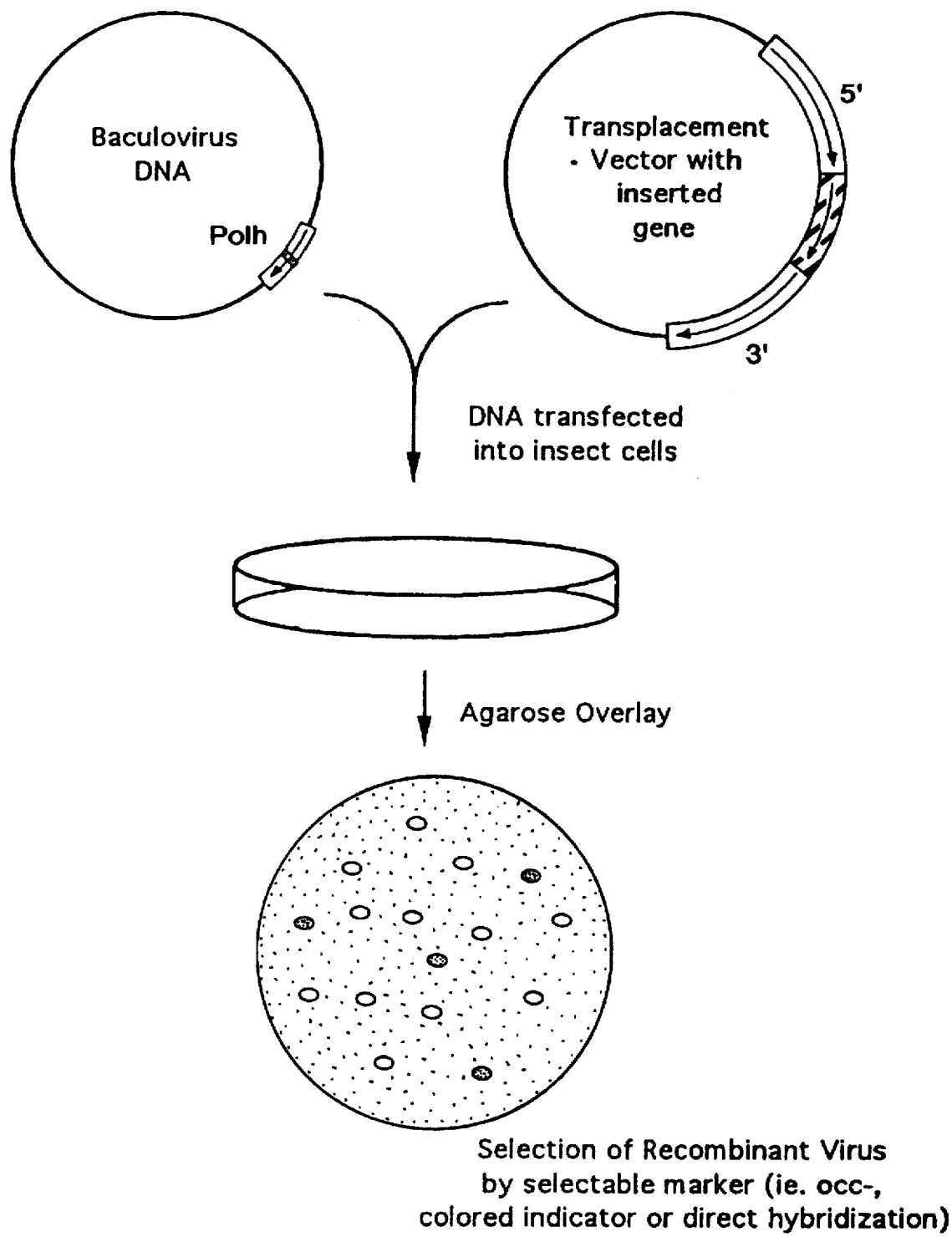
FIG. 4B depicts the method used to have the gene inserted into the virus.
Figure 4C:
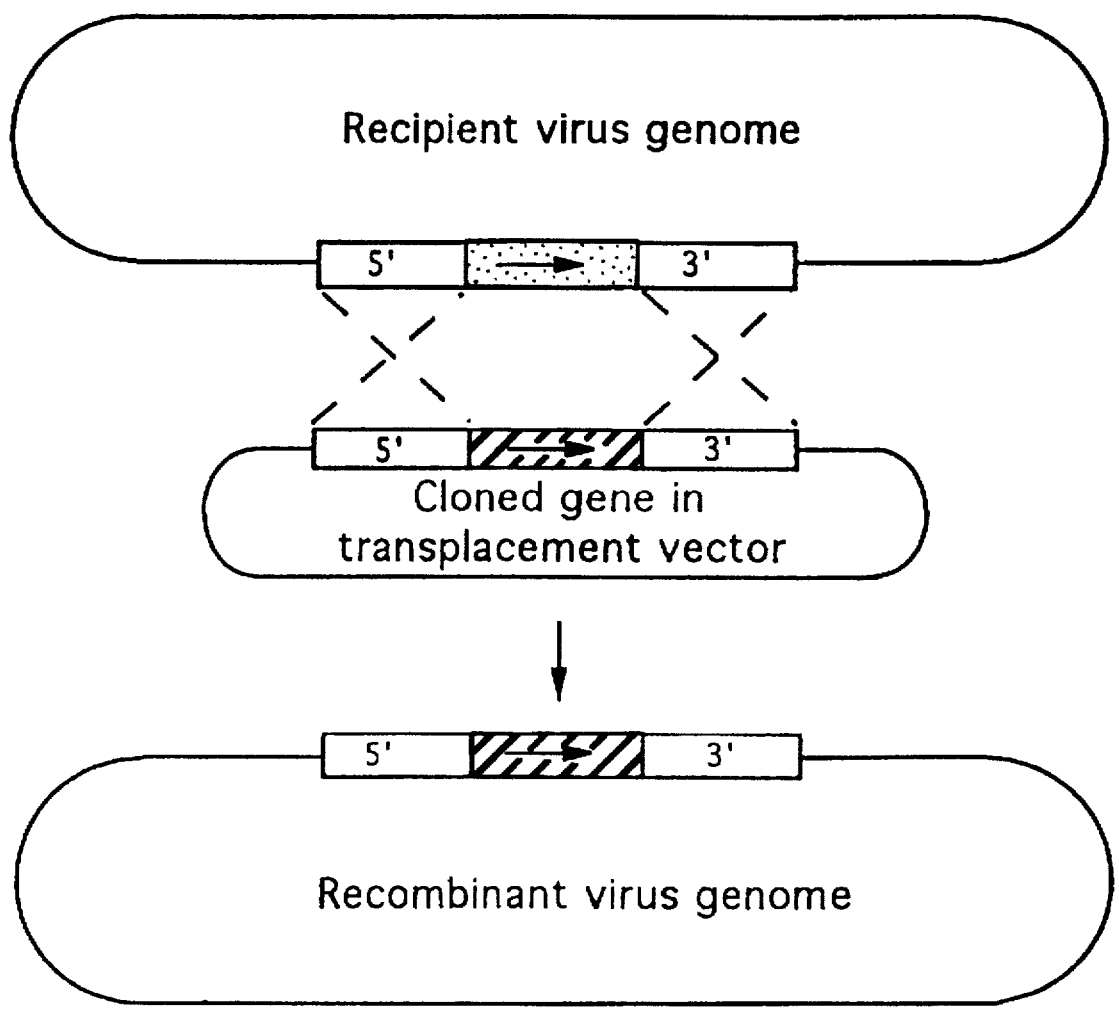
FIG. 4C demonstrates the process that occurs within the nucleus of the cultured insect cells following the introduction of transplacement vector and virus DNA.

A baculovirus transplacement vector is comprised of a piece of the recipient virus, covering the region in which the new gene will be inserted, cloned into a bacterial plasmid with a selectable marker usually a gene for antibiotic resistance. Having a bacterial plasmid backbone with an origin for replication allows the vector DNA to be maintained and propagated in a bacterial host. The antibiotic resistance allows for selection of bacteria that carrying the plasmid. Baculovirus transplacement vectors can be constructed using standard DNA cloning procedures. An example of construction of a typical transplacement vector for inserting a gene into a baculovirus is shown in FIG. 4A. In this example, the transplacement vector is constructed to insert genes at the polyhedrin gene locus. The inserted gene will replace the baculovirus polyhedrin gene and will be expressed under the control of the polyhedrin promoter. However, various other regions of the viral genome can be used as an insertion site for a foreign gene and other virus promoters can be used to drive the expression of the gene. To construct a baculovirus transplacement vector for inserting foreign genes at the polyhedrin locus, a fragment of virus DNA comprising the polyhedrin gene and its 5' and 3' flanking regions is cloned into the multiple cloning site of a bacterial plasmid that carries a gene for ampicillin resistance (FIG. 4A). The polyhedrin promoter region is left intact in the plasmid and the polyhedron coding region is cut out and replaced with a multiple cloning site to facilitate the cloning of foreign genes. The gene to be inserted into the virus is then cloned into the multiple cloning site of the transplacement vector, using standard methods, under the transcriptional control of the polyhedron promoter. To insert the gene into the virus the transplacement vector DNA is cotransfected along with virus DNA into insect cells that can replicate the virus (FIG. 4B). In order to identify plaques, agarose is added to the tissue culture medium to a final concentration of 0.5% so that the medium forms a solid overlay. This limits virus spread between cells so that plaques, small foci of infected cells, can be identified. For generating AcMNPV recombinants the SF21 cell line is typically used. Recombinant viruses are generated when the transplacement vector carrying the gene to be inserted recombines with the viral genomic DNA by homologous recombination within common DNA sequences in the flanking regions, resulting in allelic replacement of the gene between the homologous flanking sequences (FIG. 4C). Thus the new gene is inserted at a specific locus in the viral genome, in this example the polyhedron gene locus. Recombinant viruses can be identified by various methods. In this example polyhedron negative plaques were selected, a trait that can be easily discriminated visually. Alternatively, recombinants can be selected by hybridization to the inserted gene or by another selectable marker that can be incorporated into either the transplacement vector or recipient virus. A typical selectable marker used for this purpose was the lacZ gene from the bacterium *Escherichia coli*, that encodes the enzyme β-galactosidase. If a colorimetric substrate for the enzyme such as 5-bromo-4-chloro-3-indolyl-β-D-galactosidase (X-gal) is added to the growth media, when the lacZ gene is expressed, the β-galactosidase enzyme is synthesized which will cleave the X-gal resulting in a color change from clear to blue. Recombinant baculovirus technology is well established and transplacement vectors for generating recombinant baculoviruses for high-level expression of foreign genes are available commercially or from various research laboratories. Most of these are for insertion of genes into either the polyhedron or p10 gene loci of AcMNPV. For insecticidal use the p25.7 gene could be inserted in the polyhedron locus or elsewhere in the genome, however it would be beneficial to leave the polyhedron gene intact since this gene encodes a protein that protects the virus. There are several available transplacement vectors that facilitate construction of a recombinant AcMNPV virus that is polyhedron positive. These include pAcUW2A and pAcUW2B (Weyer, U., et al., J. Gent. Virol. 71:1525–1534 (1990)) and pSynXIV VI+, pSynXIV VI+X3, pSynVI+wtp, pLSXIV VI+, and pLSXIV VI+X3 (Wang, X., et al, Gene 100:131–137 (1991)). Each of these transplacement vectors has an intact polyhedron gene as well as a second promoter and cloning site. Each of these transplacement vectors is designed for recombination within the polyhedron locus. Typically the recipient virus used for generating recombinants with these vectors is lacking the polyhedron gene. Alternatively to obtain occlusion positive viruses, genes can be inserted and a different locus in the viral genome leaving the polyhedron gene intact. Transplacement vectors for inserting genes in the p10 locus of AcMNPV (Vlak, J. M., et al, Expression of cauliflower mosaic virus gene I using a baculovirus vector based upon the p10 gene and a novel selection method (1990); Weyer, U., et al, J. Gen. Virol. 71:1525–1534 (1990)) result in occlusion positive viruses and are also available from various research laboratories. For inserting the p25.7 gene into most baculoviruses other than AcMNPV suitable transplacement vectors would need to be constructed, using the principles discussed above.

Figure 5A:
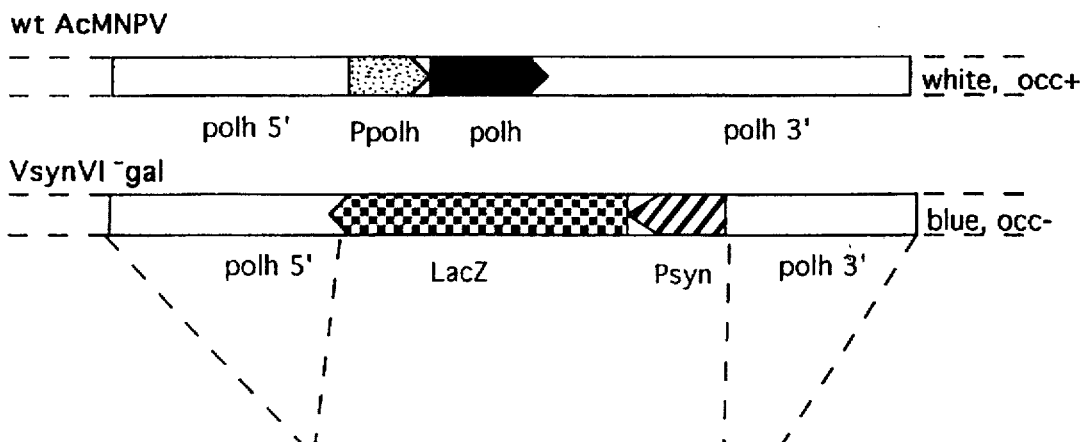
FIG. 5A shows the polyhedron gene region of wt AcMNPV and the same region of a recombinant AcMNPV, Vsyn-gal, used as a recipient virus.
Figure 5B:
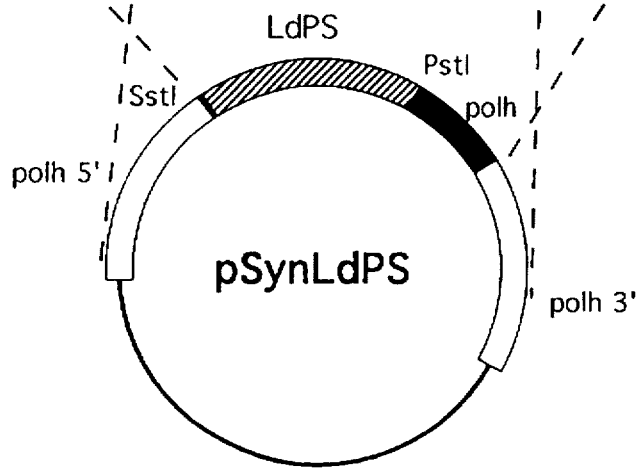
FIG. 5B shows a diagram of pSynLdPS an AcMNPV transplacement vector in which a DNA fragment from LdMNPV (PstI-SstI, 43.3–44.6 map units) has been inserted.
Figure 5C:
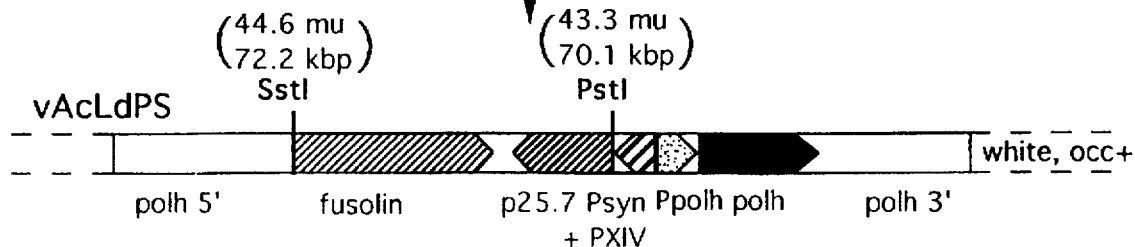
FIG. 5C diagrams the polyhedron region of the recombinant AcMNPV, vAcLdPS, that resulted from recombination between pSynLdPS and VsynVI-gal.

Because ingestion of the occluded form of nuclear polyhedrosis viruses is the normal route of infection for insect larvae, a recombinant virus that was polyhedron positive was constructed. An occlusion positive recombinant virus permits testing the ability of p25.7 to effect the host specificity of AcMNPV when the recombinant virus is eaten by caterpillars. Construction of the recombinant virus was achieved using standard recombinant DNA technology and procedures developed for baculovirus expression vectors (Summers, M. D. et al., A manual of methods for baculovirus vectors and insect culture procedures. Texas Agricultural Experiment Station Bulletin No. 1555 (1987)). A recombinant virus was then selected from the resulting virus progeny by plaque assay. To construct an occlusion positive AcMNPV recombinant virus for testing, the transplacement vector pSynXIV VI+ (Wang, X., et al, Gene 100:131–137 (1991)), obtained from L. K. Miller, University of Georgia, was used to insert the p25.7 gene into AcMNPV. The PstI-SstI fragment located 43.3–44.6 map units on the LdMNPV physical map was cleaved from the Bluescript vector using restriction enzymes PstI and SstI and ligated into the PstI and SstI sites of the transplacement vector pSynXIV VI+ to generate transplacement plasmid pSynLdPS (FIG. 5B). The recipient virus was VsynVI-gal (Wang, X., et al, Gene 100:131–137 (1991)), an AcMNPV recombinant virus in which the polyhedron gene and its promoter have been replaced by the *E. coli* lacZ gene under the control of a synthetic baculovirus gene promoter, Psyn (FIG. 5A). Vsyn VI-gal does not produce polyhedra, but does produce the *E. coli* enzyme β-galactosidase. When Xgal is added to media containing 0.5% agarose that was applied as an overlay on VsynVI-gal-infected cell monolayers viral plaques were formed that are blue and occlusion negative. Because pSynLdPS carries an intact AcMNPV polyhedrin gene with its cognate promoter as well as the PstI-SstI gene fragment from LdMNPV, homologous recombination eliminates the *E. coli* lacZ gene and restores the AcMNPV at the polyhedrin gene locus (FIG. 5C). pSynLdPS and VsynVI-gal DNA and was transfected iinto SF21 cells using a calcium phosphate precipitation procedure (Summers, M. D. and Smith, G. E., A manual of methods for baculovirus vectors and insect culture procedures. Texas Agricultural Experiment Station Bulletin No. 1555 (1987)). Briefly, SF21 cells growing in TC100 medium (Life Technologies, Bethesda, Md.), supplemented with 10% fetal bovine serum, were seeded into 60 mm tissue culture plates, $2\times10^6$ cells/plate, and allowed to attach for 30 minutes to form subconfluent monolayers. The medium was then removed and replaced with 0.75 ml Grace's medium (Life Technologies, Bethesda, Md.), supplemented with 10% fetal bovine serum. VSyn VI-gal was linearized by cleavage with Bsu36I, which cleaves at a single site within the lacZ gene, in order to maximize homologous recombination. pSynLdPS DNA, 2 μg, and VSynVI-gal DNA, 1 μg, were mixed in sterile transfection buffer to a final volume of 0.75 ml. Transfection buffer is 25 mM HEPES, pH 7.1; 140 mM NaCl; 125 mM $CaCl_2$. The DNA in transfection buffer is added dropwise to the cell monolayers and the plates are incubated at 27° C. for 4 hours. Following the 4 hour incubation the transfection buffer and medium are removed from the cell monolayers and the monolayer is washed 1× with TC100 medium. The cells are then fed with 4 ml of TC100 medium supplemented with 10% fetal bovine serum and incubated at 27° C. for four days. The supernatants from these transfections are diluted, serial dilutions from $10^{-1}$ to $10^{-6}$, and 500 μl of each dilution is used to infect a monolayer of SF21 cells, $2\times10^6$ cells/60 mm tissue culture plate. After removing the medium from the cell monolayers, dilutions are added dropwise and then the plates are rocked gently for an hour. The diluted transfection supernatants are then removed and replaced with TC100 supplemented with 10% fetal bovine serum and agarose to a final concentration of 0.5%. Recombinant viruses were selected as white occlusion positive plaques among a background of blue occlusion negative plaques. Recombinant viruses were harvested from the plates by gentle aspiration into a pipette. The virus plaques were resuspended in tissue culture medium and purified by serial dilution followed by two additional rounds of plaque purification. To determine that the PstI-SstI fragment from LdMNPV was properly inserted, DNA was isolated from recombinants and analyzed by digestion with restriction endonucleases followed by separation of the DNA fragment by agarose gel electrophoresis. Recombinants were characterized by the appearance of a unique XhoI restriction fragment from LdMNPV corresponding to approximately 43.9–44.43 map units on the LdMNPV physical map (see FIG. 2C). The recombinant virus, vAcLdPS, was an AcMNPV virus that has been altered at the polyhedron locus such that the polyhedron gene and its promoter were intact and p25.7 has been inserted under the control of its own promoter as well as under the control of tandem synthetic promoters, Psyn and PXIV (FIG. 5C). A second LdMNPV gene, fusolin, and its promoter region is also inserted in this construct.

EXAMPLE 3

Replication of vAcLdPS in non-permissive hosts.

The baculovirus AcMNPV does not replicate in the gypsy moth cell line, Ld652Y, or in gypsy moth larvae. A recombinant AcMNPV, vAcLdPS, that has a 2.1 kbp fragment of LdMNPV from 43.3–44.6 map units on the LdMNPV physical map (FIG. 2C) comprising a host range gene, the p25.7 gene, and the LdMNPV fusolin gene inserted adjacent to the AcMNPV polyhedron gene was constructed (described in Example 2). In nuclear polyhedrosis virus-infected lepidopteran cell lines budded virus is shed into the cell culture media and occluded viruses are assembled in the cell nuclei. Stocks of vAcLdPS budded virus were prepared by collecting cell culture media from vAcLdPS-infected insect cells between two and four days post infection and removing cells by low speed centrifugation. Occluded vAcLdPS was prepared by harvesting the infected cells and releasing the polyhedra from the cells by treatment with detergent (0.5% sodium dodecyl sulfate) followed by washes with sodium chloride (0.5 molar) and distilled water to remove the detergent. Polyhedra were recovered by centrifugation after each wash. Viruses were propagated in SF21 cells, a host cell line for AcMNPV. The number of infectious budded viruses in the stock was determined by plaque assay on SF21 cells. In brief, serial dilutions of the virus stock was made in tissue culture media. SF21 cells were seeded into 60 mm tissue culture plates and allowed to attach and form a subconfluent monolayer. Aliquots of diluted virus (0.5 ml/plate) were added to the plates dropwise and the plates were gently rocked for a period of one hour to allow the virus to attach to and enter the cells. Following virus attachment the monolayers were washed with tissue culture media and an overlay of tissue culture media containing 0.5% agarose was applied over the cell monolayer. After five days the number of virus plaques were counted and the amount of virus, the number of plaque forming units per ml of stock solution, in the stock was calculated. The number of polyhedra in the polyhedra preparation were determined by counting serially diluted stocks directly using a microscope and a hemocytometer, a counting chamber for cells and other microscopic samples.

Figure 6A:
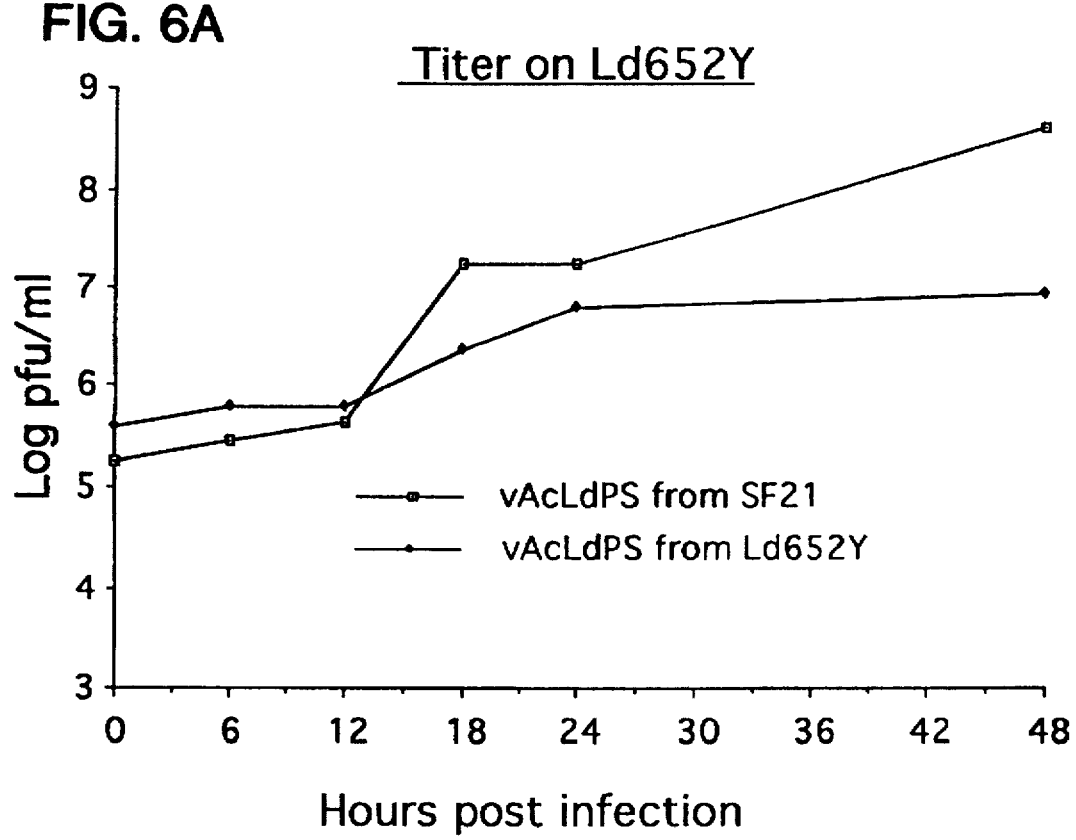
FIG. 6A shows virus titers on Ld652Y cells.
Figure 6B:
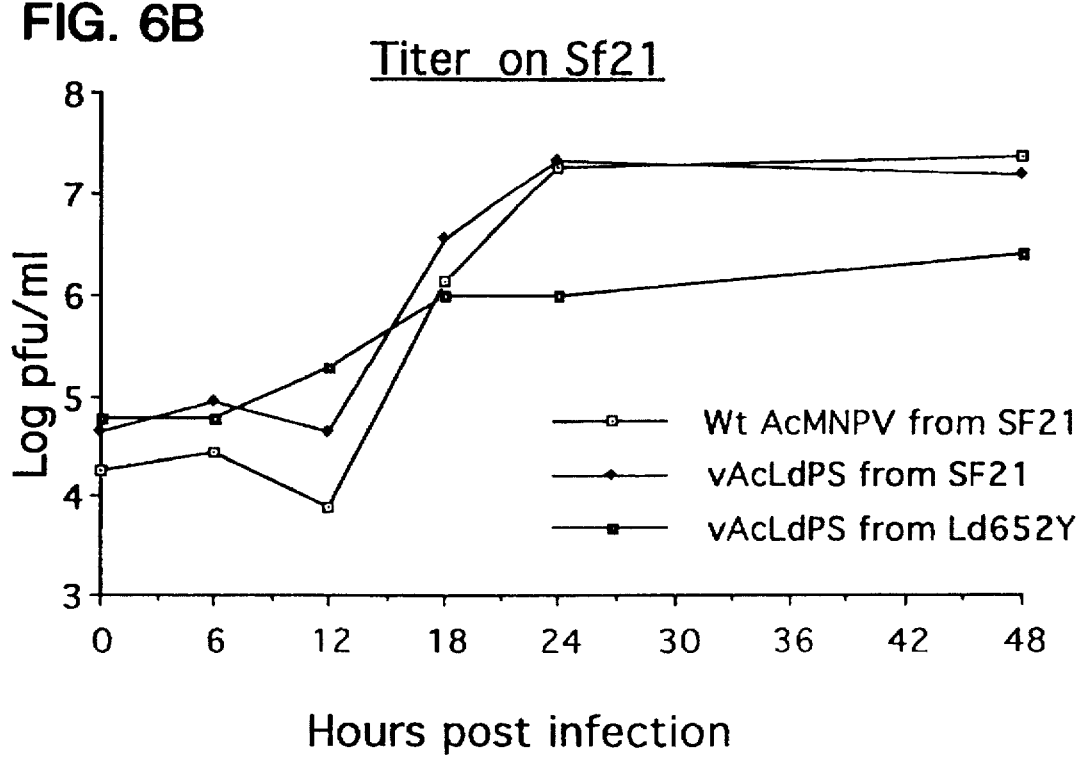
FIG. 6B shows virus titers on SF21 cells.

To test vAcLdPS in Ld652Y cells, monolayers of cells were infected with vAcLdPS at a multiplicity of infection of 10 plaque forming units per cell. vAcLdPS replicates in Ld652Y cells as evidenced by the production of polyhedra in the nucleus of cells by 24 hours post infection and the presence of infectious virus in the supernatants. Production of budded virus in Ld652Y and SF21 cells was compared by infecting monolayers of both cell lines with equal amounts of virus. Cell culture media was collected at various times after infection and budded virus production was evaluated by titering the virus in the supernatants by plaque assay on both Ld652Y and SF21 cells (FIG. 6). vAcLdPS budded virus production was equivalent to wt AcMNPV virus production on SF21 cells. However vAcLdPS production in Ld652Y cells was approximately 10 fold less than in SF21 cells. The reason less vAcLdPS budded virus is produced in Ld652Y cells than in SF21 cells is not clear, but it may be due to the slower growth rate of the Ld652Y cells. Because AcMNPV wildtype virus cannot replicate in Ld652Y cells it is not possible to compare wildtype and recombinant virus as in SF21 cells.

In feeding experiments, early second instar gypsy moth larvae were fed $3.8 \times 10^5$ PIBs in a single dose applied to a diet plug. Forty-eight (48) larvae that consumed the entire dose were transferred to fresh media and observed until they died or until the experiment was terminated 45 days after infection. No mortality was observed until 24 days after infection. Only larvae in which PIBs were observed were scored as virus mortality.

TABLE 2

| Infection of gypsy moth larvae with vAcLdPS | | |
|---|---|---|
| | vAcLdPS | Control |
| virus mortality* | 10 | — |
| death other cause | 9 | 14 |
| Total Mortality | 19 | 14 |
| % mortality VIRUS | 20.8% | 0% |
| % mortality TOTAL | 39.6% | 29.2% |

*Presence of vAcLdPS confirmed by restriction endonuclease digestion of DNA from PIBs isolated from larval cadavers.

Although the larval mortality from recombinant virus was not 100%, this is the first evidence that the transfer of a single baculovirus gene from one virus to another is able to alter both the in vitro and in vivo host range of the recipient virus.

It is intended that the foregoing description be only illustrative of the present invention and that the present invention be limited only by the hereinafter appended claims.

I claim:

1. An isolated segment of DNA of a first nuclear *polyhedrosis baculovirus* encoding a protein homologous to the protein sequence shown in in SEQ ID NO:2 so as to provide infection in *Lymantria dispar* cells or larvae when the DNA is incorporated into a second nuclear *polyhedron baculovirus* which is unable to infect the *Lymantria dispar* cells or larvae.

2. The DNA of claim 1 as set forth in SEQ ID NO:1.

3. The DNA of claim 1 isolated from virus LdMNPV as the first nuclear *polyhedrosis baculovirus*.

4. An isolated segment of DNA which is a gene of a nuclear *polyhedrosis baculovirus* encoding a 25.7 kdal protein wherein the DNA is contained in plasmid pBSLdPd deposited as ATCC 97061 and provides infection in *Lymantria dispar* cells or larvae when the DNA is incorporated into a second nuclear *polyhedron baculovirus* which is unable to infect the *Lymantria dispar* cells or larvae.

5. A recombinant vector carrying an isolated segment of DNA of a first nuclear *polyhedrosis baculovirus* encoding a protein homologous to the protein sequence shown in SEQ ID NO:2 so as to provide infection in *Lymantria dispar* cells or larvae when the DNA is incorporated into a second nuclear *polyhedrosis baculovirus* which is unable to infect the *Lymantria dispar* cells or larvae.

6. The vector of claim 5 containing the DNA as set forth in SEQ ID NO:1.

7. The vector of claim 5 containing DNA isolated from virus LdMNPV as the first nuclear polyhedrosis virus.

8. A recombinant vector containing a segment of an isolated segment of DNA which is a gene of a nuclear polyhedrosis virus encoding a 25.7 kdal protein wherein the DNA is contained in plasmid pBSLdPd deposited as ATCC 97061 and provides infection in *Lymantria dispar* cells or larvae when the DNA is incorporated into a nuclear polyhedrosis virus which is unable to infect the *Lymantria dispar* cells or larvae.

9. A nuclear polyhedrosis virus containing a segment of DNA encoding a protein homologous to the protein sequence shown in SEQ ID NO:2 so as to provide infection in *Lymantria dispar* cells or larvae when the DNA is incorporated into a second nuclear polyhedrosis virus which is unable to infect in the *Lymantria dispar* cells or larvae.

10. The nuclear polyhedrosis virus of claim 9 wherein the DNA is as set forth in SEQ ID NO:1.

11. The nuclear polyhedrosis virus of claim 9 wherein the DNA is isolated from LdMNPV as the first nuclear polyhedrosis virus.

12. A recombinant nuclear polyhedrosis virus containing DNA which is a gene of a first nuclear polyhedrosis virus encoding a 25.7 kdal protein wherein the DNA is contained in plasmid pBSLdPd deposited as ATCC 97061 and provides infection in *Lymantria dispar* cells or larvae when the DNA is incorporated into a second nuclear polyhedrosis virus which is unable to infect the *Lymantria dispar* cells or larvae.

13. A method of infecting *Lymantria dispar* cells or larvae which comprises exposing the cells or larvae to a recombinant nuclear polyhedrosis virus containing a segment of DNA of a first nuclear polyhedrosis virus encoding a protein homologous to that as set forth in SEQ ID NO:1 so as to provide infection in *Lymantria dispar* cells or larvae when the DNA is incorporated into a second nuclear polyhedrosis virus, which is unable to infect the *Lymantria dispar* cells or larvae.

14. The method of claim 13 wherein the DNA is as set forth in SEQ ID NO:1.

15. The method of claim 13 wherein the DNA is isolated from virus LdMNPV as the first nuclear polyhedrosis virus.

16. A method of inhibiting *Lymantria dispar* cells or larvae which comprises exposing the cells or larvae to a recombinant nuclear polyhedrosis virus containing a segment of DNA which is a gene of a first nuclear polyhedrosis virus encoding a 25.7 kdal protein wherein the DNA is contained in plasmid pBSLdPd deposited as ATCC 97061 and provides infection in the *Lymantria dispar* cells or larvae when the DNA is incorporated into a second nuclear polyhedrosis virus which is unable to infect the *Lymantria dispar* cells or larvae.

17. The method of claim 16 wherein the second nuclear polyhedrosis virus is *Autographa californica* nuclear polymer polyhedrosis virus.

18. The DNA as set forth in SEQ ID NO:1.

19. A recombinant vector containing the DNA as set forth in SEQ ID NO:1.

20. A recombinant nuclear polyhedrosis virus containing the DNA as set forth in SEQ ID NO:1 wherein the DNA enables the nuclear polyhedrosis virus to infect cells or larvae of *Lymantria dispar*.

21. A method of infecting *Lymantria dispar* cells or larvae which comprises exposing the cells or larvae to a recombinant nuclear polyhedrosis virus containing a segment of DNA as set forth in SEQ ID NO:1, wherein the DNA enables the cells or larvae to infect cells or larvae of *Lymantria dispar*.

* * * * *

UNITED STATES PATENT AND TRADEMARK OFFICE
CERTIFICATE OF CORRECTION

PATENT NO. : 5,639,454

DATED : June 17, 1997

INVENTOR(S) : Suzanne M. Thiem

It is certified that error appears in the above-indentified patent and that said Letters Patent is hereby corrected as shown below:

On the title page: Item [56]

under "Other Publications" second column, last line, "mehtod" should be --method--.

"In The Abstract", line 11, "california" should be --californica--.

Column 6, Table 1, 1st column "ACMNPV+C-77" should be --AcMNPV+C-77 --; and "ACMNPV+C-38" should be --AcMNPV+C-38 --.

Column 8, line 31, "carrying" should be --carries--.

Column 9, line 30, "Weyer, U., et al., J. Gert. Virol" should be --Weyer, U., et al., J. Gen. Virol--.

Column 10, line 18, "polyhedrin" should be --polyhedron--.

Column 10, line 21, "polyhedrin" should be --polyhedron--.

Column 10, line 22, "transfected iinto" should be --transfected into--.

Column 15, line 65 (Claim 1), after "shown", "in", second occurrence, should be deleted.

Column 17, line 9 (Claim 5), "polyhedrosis baculovirus" should be --polyhedrosis virus--.

Column 17, line 12 (Claim 5), "polyhedrosis baculovirus" should be --polyhedrosis virus--.

UNITED STATES PATENT AND TRADEMARK OFFICE
CERTIFICATE OF CORRECTION

PATENT NO. : 5,639,454
DATED : June 17, 1997
INVENTOR(S) : Suzanne M. Thiem

It is certified that error appears in the above-indentified patent and that said Letters Patent is hereby corrected as shown below:

Column 18, lines 26 and 27 (Claim 17), "nuclear polymer polyhedrosis" should be --nuclear polyhedrosis--.

Signed and Sealed this

Sixteenth Day of September, 1997

Attest:

BRUCE LEHMAN

Attesting Officer

Commissioner of Patents and Trademarks